(12) United States Patent
Yang et al.

(10) Patent No.: US 6,509,562 B1
(45) Date of Patent: Jan. 21, 2003

(54) SELECTIVE PHOTO-IONIZATION DETECTOR USING ION MOBILITY SPECTROMETRY

(75) Inventors: Wenjun Yang, Sunnyvale, CA (US); Peter C. Hsi, Fremont, CA (US)

(73) Assignee: RAE Systems, Inc., Sunnyvale, CA (US)

( * ) Notice: Subject to any disclaimer, the term of this patent is extended or adjusted under 35 U.S.C. 154(b) by 0 days.

(21) Appl. No.: 09/397,625

(22) Filed: Sep. 16, 1999

(51) Int. Cl.[7] ............................ B01D 59/44; H01J 49/00
(52) U.S. Cl. .................................... 250/287; 250/423 P
(58) Field of Search .......................... 250/423 P, 286, 250/287, 288

(56) References Cited

U.S. PATENT DOCUMENTS

| | | | | |
|---|---|---|---|---|
| 2,768,304 A | * | 10/1956 | Wells ........................ | 250/287 |
| 5,338,931 A | * | 8/1994 | Spangler et al. ......... | 250/423 P |
| 5,393,979 A | * | 2/1995 | Hsi ......................... | 250/423 P |
| 5,457,316 A | * | 10/1995 | Cohen et al. ............... | 250/286 |
| 5,968,837 A | * | 10/1999 | Doring et al. ............. | 250/288 |

* cited by examiner

*Primary Examiner*—Bruce Anderson
(74) *Attorney, Agent, or Firm*—Skjerven Morrill LLP

(57) ABSTRACT

A photo-ionization detector (PID) employs combinations of ion mobility spectrometry, ionization energy discrimination, and chemical filtering to identify the presence and quantity of specific gases. One such PID introduces a gas sample into an ionization chamber at an end of a drift tube. UV light from a PI source ionizes ionizable molecules contained in the gas sample. The PI source includes either multiple UV lamps, each having a specific energy level for discriminating between potential constituents of the gas sample or one multiple-energy level UV lamp with different light bandwidth window zones and a zone selector. A shutter grid separates the ionization chamber from the drift tube. When the shutter grid is open, an electric field in the drift tube attracts ions that travel against the flow of a drift gas until a collector electrode at the end of the drift tube captures the ions. A time required for the ions to travel the length of the drift tube is characteristic of the type of ion. Thin mesh electrodes in the drift tube sustain a uniform electric field so that groups of ions traveling down the drift tube to create well defined current pulses at the collector electrode.

17 Claims, 7 Drawing Sheets

SELECTIVE PHOTO-IONIZATION DETECTOR USING ION MOBILITY SPECTROMETRY

BACKGROUND

1. Field of the Invention

This invention relates to photo-ionization detectors that use ion mobility spectrometry, ionization potential discrimination, and/or chemical filtering to detect, identify, and measure quantities of selected gases.

2. Description of Related Art

Conventionally, photo-ionization detectors (PIDs) measure the concentration of ionizable gases in a sample by measuring the number of ions created when UV light passes through the sample. Generally, PIDs perform "broadband" measurements that do not provide specific information that identifies the particular gas in the sample because the UV light ionizes all types of gases having ionization potentials below the maximum photon energy of the UV light and all of the ions are measured as a group. However, co-owned Pat. App. Ser. No. 09/330,522, now U.S. Pat. No. 6,320,388, issued on Nov. 20, 2001, entitled "Multiple Channel Photo-Ionization Detector for Simultaneous and Selective Measurement of Volatile Organic Compounds", which is hereby incorporated by reference in its entirety, describes a PID employing a UV lamp having separate window sections that pass UV light with different energy spectra. Separate measurements of ion currents caused by the different UV light spectra can identify a range for the ionization potential of gases in a sample, and the identified ionization potential indicates chemical composition of the ionizable gas. However, gases having nearly identical ionization potentials may be difficult to distinguish using such techniques.

Ion mobility spectrometry (IMS) distinguishes compounds by gas phase ion mobilities. Conventionally, for IMS, a radioactive source such as Ni-63 ionizes molecules in a sample gas, and an electric field in a drift tube causes the ions to travel down the drift tube against the flow of a drift gas. Different types of ions typically reach the end of the drift tube at different times depending, for example, on the mass, the size, and the charge of the ion. A collector electrode at the end of the drift tube collects the ions which thereby generate one or more current pulses. Specific types of ions from the sample gas can be identified from the time periods measured for the ions to travel the length of the drift tube.

The use of a radioactive source, which requires licensing and special waste disposal, limits the acceptance of ion mobility spectrometry in commercial products. Further, radioactive sources tend to ionize a large class of compounds including common components of air such as oxygen, nitrogen, and water vapor. These ions can in turn react with other molecules and ions in the sample to generate a relatively large number of ion species. In general, the ion species have different mobilities and reach the collector at different times. However, the current pulses corresponding to the different ion mobilities can overlap, making difficult the discrimination or identification of a particular ion type.

A further problem in discriminating the various ion signals is non-uniformity of the electric field in the drift tube. In particular, a conventional drift tube includes a set of conducting rings that are in the walls of a cylindrical tube. Each ring has a different voltage level so that an electric field in the drift tube is directed from the rings at higher voltages toward the rings at lower voltages. With this configuration, the electric field is relatively weak along an axis that passes through the centers of the rings and increases radially toward the rings. Accordingly, ions traveling near the axis experience the weaker electric field and correspondingly have a lower average drift velocity. Ions traveling near the walls of the drift tube thus reach the collector electrode before ions traveling near the axis of the drift tube, and the signal peak corresponding to a particular type of ion is spread out in time by at least the difference in the travel time that the non-uniform electric field causes. Also, the electric field in each region that is surrounded by a ring has a relatively weak electric field because the surrounding ring has a uniform electric potential, while regions between the rings have a relatively strong electric field caused by the drop in electric potential between the rings. This causes axial variations in the electric field. Both the radial and axial variation in the electric fields broaden signal peaks and make different types of ions more difficult to distinguish.

SUMMARY

In accordance with an embodiment of the invention, a photo-ionization detector (PID) uses one or more UV lamps to ionize a gas for an ion mobility measurement. Each lamp or window zone of a lamp produces light having a different UV spectrum and ionizes different sets of ionizable gas. Ion mobility measurements using the different UV spectra provide quantitative information about the ion types. Thus, this PID can distinguish different gases based on the ionization potential and ion mobility. The PID can identify specific chemicals in trace amounts. Accordingly, unlike conventional PID technology, which only provides broadband detection, PIDs disclosed here can not only realize broadband detection, but also selectively identify the presence and amount of specific gaseous chemicals.

From another perspective, embodiments of the invention provide an improved ion mobility spectrometer that employs one or more electrodeless UV lamps and does not require a radioactive element UV photo-ionization generates fewer ion species from a sample than would chemical ionization by a radioactive source and is easily tunable for selection of a particular ionization potential. The UV lamps are also more convenient to handle and use than is a radioactive source.

A further improvement of ion mobility spectrometers arises in embodiments of the invention that employ electrode configurations yielding a more uniform electric field in a drift tube. One such drift tube uses mesh plate electrodes rather than conventional hollow cylindrical electrodes, to form the electric drift field. With the mesh plate electrodes, the transformation efficiency of voltage to intensity of electric filed is much higher than that in the conventional configuration because in the new configuration the electric field is between the electrodes, rather than beside the electrodes as in the conventional configuration. The mesh electrodes reduce the radial non-uniformity in electric fields in drift tubes. The mesh electrodes also reduce the voltage required for a suitable electric field in a drift tube and hence benefit portable detectors.

In addition, the electrodes are very thin (for example, less than 1 mm) to improve axial uniformity of the electric field. In conventional drift tubes, relatively thick cylindrical electrodes cause an electric field across the thickness of each electrode to be weak when compared to the electric field between adjacent electrodes. The electric field is thus more uniform both radially and axially than the electric field in the traditional drift tubes, and the more uniform electric field reduces the total peak broadening. As a result, the detector has better resolution of the signal peaks and improved selectivity. Additionally, the reduction of peak broadening increases the peak heights of the signals and thereby improves sensitivity.

In accordance with another aspect of the invention, a tunable UV spectrum permits discrimination of chemical species according to differences in ionization potentials. One method for producing tunable photo-ionization uses multiple photo-ionization lamps with different maximum photon energies, for example, four UV lamps with maximum photon energies of 8.4, 9.8, 10.6, and 11.7 eV, respectively. Another method of producing tunable photo-ionization uses one UV lamp having multiple window zones and a zone selector. Each window zone passes a different spectrum of UV light. For example, the window of the lamp can include four different crystals having optical bandwidths with maximum photon energies of about 8.4 eV, 9.8 eV, 10.6 eV, and 11.7 eV, respectively. The zone selector chooses one zone of the window each time to allow a specified UV light spectrum to illuminate the sample and ionize the components of the sample. A sequence of ion mobility measurements uses different UV spectra to ionize the sample and measures drift times for the ions that each UV spectrum generates. Comparison of the peaks generated using different UV spectra can identify and approximate ionization potentials corresponding to specific peaks. In this manner, components having different ionization potentials are selectively ionized and discriminated.

In accordance with an aspect of the invention, a photo-ionization detector (PID) employs combinations of ion mobility spectrometry, ionization energy discrimination, and chemical filtering to identify the presence and quantity of specific gases. FIG. 1 shows a PID in accordance with an embodiment of this invention. The PID 10 includes an ionization chamber 14 and a drift tube 16. In an exemplary embodiment of the invention, ionization chamber 14 is a cylindrical about 20 mm in diameter and about 40 mm long, and drift tube 16 is also cylindrical with a diameter of about 20 mm but is about 100 mm long. The walls of ionization chamber 14 and drift tube 16 are made of a material such as Teflon, glass, or ceramics, which is resistant to chemical reactions with ions that are in ionization chamber 14 and drift tube 16 during operation of PID 10.

BRIEF DESCRIPTION OF THE DRAWINGS

Use of the same reference symbols in different figures indicates similar or identical items.

DETAILED DESCRIPTION

Figure 1:
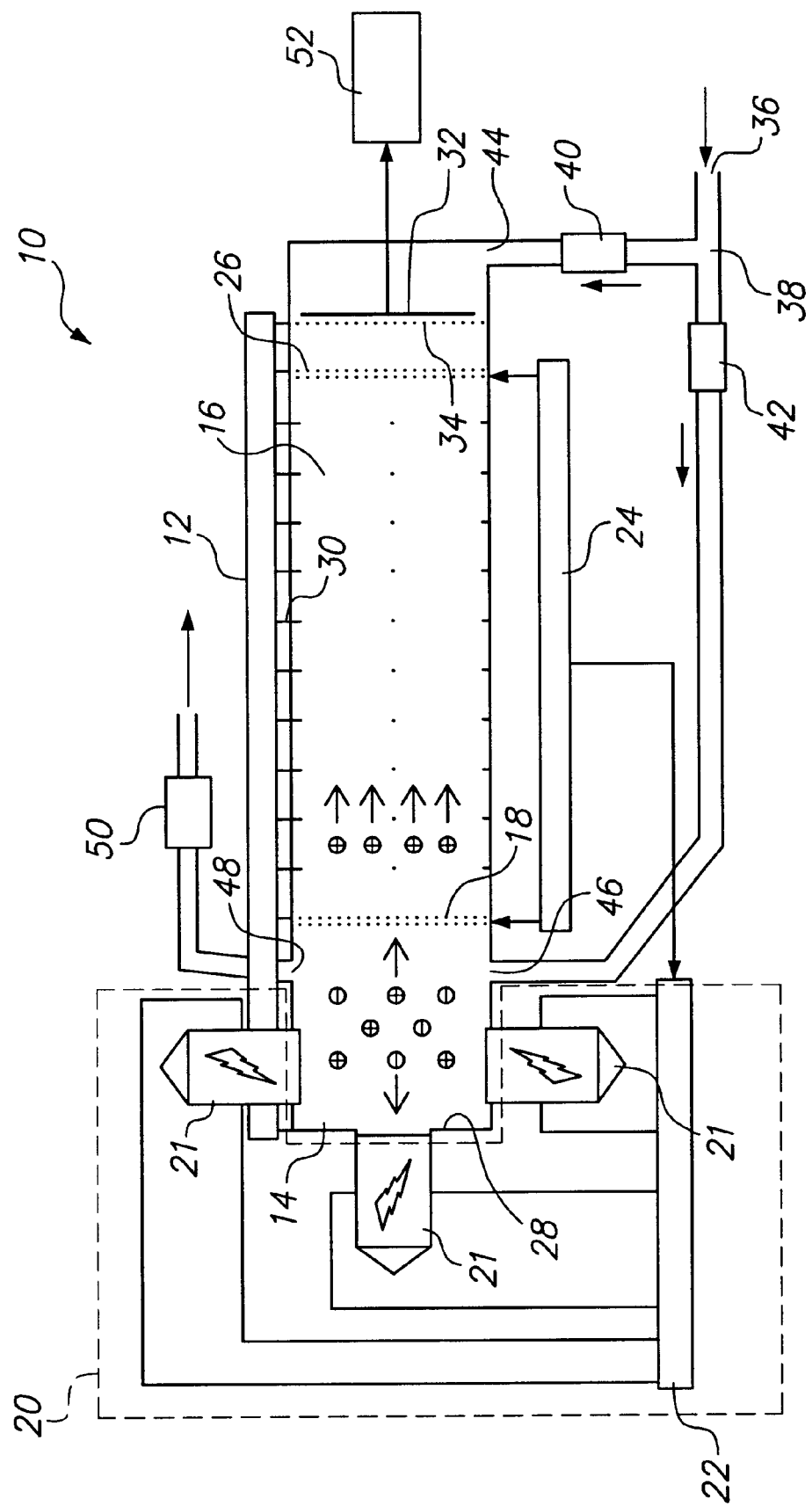
FIG. 1 is a block diagram of a photo-ionization detector including a chemical filter, multiple UV lamps, and an ion mobility spectrometer in accordance with an embodiment of the invention.

In accordance with an aspect of the invention, a photo-ionization detector (PID) employs combinations of ion mobility spectrometry, ionization energy discrimination, and chemical filtering to identify the presence and quantity of specific gases. FIG. 1 shows a PID 10 in accordance with an embodiment of this invention. The PID 10 includes an ionization chamber 14 and a drift tube 16. In an exemplary embodiment of the invention, ionization chamber 14 is a cylindrical about 20 mm in diameter and about 40 mm long, and drift tube 16 is also cylindrical with a diameter of about 20 mm but is about 100 mm long. The walls of ionization chamber 14 and drift chamber 16 are made of a material such as Teflon, glass, or ceramics, which is resistant to chemical reactions with ions that are in ionization chamber 14 and drift tube during operation of PID 10.

A sample gas inlet 46 introduces a gas sample into ionization chamber 14, and a photo-ionization source 20 mounted on ionization chamber 14 illuminates the sample gas with UV light capable of ionizing molecules such as molecules of volatile organic compounds. In FIG. 1, source 20 includes multiple UV lamps 21 mounted on ionization chamber 14. Each lamp 21 provides a different spectrum of UV light and particularly has a maximum photon energy that differs from the maximum photon energy of other lamps 21. Alternatively, as described further below, photo-ionization source 20 can include a single UV lamp with a single UV spectrum or a single UV lamp having multiple window zones that provide different UV spectra. An integrated miniature AC power supply 22, for example, a high volt, 50 to 500 kHz power supply powers lamps 21 to initiate and maintain glow discharge when a controller 24 selects one of lamps 21 for a measurement. An example of a suitable AC power supply is a 1000 volt, 30 kHz fluorescent lamp power supply BXA-24259 available from JKL Components Corp. of Pacoima, Calif.

Drift tube 16 is typically cylindrical and has a series of electrodes 30, which are perpendicular to the axis in drift tube 16. A high voltage DC power supply 12 supplies a series of voltage potentials to electrodes 30 in drift tube 16 to sustain a uniform electric field directed along the axis of drift tube 16 toward collector electrode 32. DC power supply 12 typically uses a series voltage divider to apply the voltage difference in approximately equal steps to all electrodes in ionization chamber 14 and drift tube 16 to achieve a uniform electric field in drift tube 16. In the exemplary embodiment, drift tube 16 includes seven electrodes and has a drift length of about 70 mm (from an ion shutter 18 to collector electrode 32. A 2.2 kV DC power supply generates an electric field of about 200 V/cm from repelling electrode 28 to collector electrode 32. In this configuration, typical drift times for ions are between 8 and 16 ms.

A drift gas flows through drift tube 16 in a direction opposite to the electric field (i.e., opposite the drift direction of the ions in drift tube 16). A pneumatic system controls introduction of the sample gas into ionization chamber 14 and drift gas into drift tube 16. The pneumatic system includes an inlet for a sample gas. A splitter 38 adjacent inlet 36 directs gas toward ionization chamber 14 and toward drift tube 16. The path to ionization chamber 14 includes an optional chemical filtering device 42 that removes gases that may interfere with identification or measurement of any of the target chemicals. The path to drift tube 16 includes an air purifier 40 that filters the sample gas and attempts to produce clean air as the drift gas. A drift gas inlet 44 at the end of drift tube 16 admits the drift gas, which flows through drift tube 16 toward an outlet 48 in ionization chamber 14. A vacuum pump 50 downstream from outlet 48 removes the sample gas and the drift gas from ionization chamber 14.

In the exemplary embodiment of the invention, pump 50 and the sizes of inlets 44 and 46 and outlet 48 are such that the flow of drift gas through drift tube 16 is about 300 ml/min and the flow of sample gas through ionization chamber 14 is about 200 ml/min.

PID 10 is suitable for field use where the sample gas is ambient air from surroundings that may contain a low concentration of the target chemicals to be detected. However, if PID 10 is not for field use, the sources for the drift gas and the gas sample may be different. In this case, splitter 38 and air purifier 40 may not be required. Further, PID 10 can be combined with a gas chromatographic (GC) column that provides the gas sample. With a GC column, vacuum pump 50 is not needed for introduction of the gas sample because the effluent from the GC column can be directly injected into ionization chamber 14 through sample inlet 46.

A controller 24 directs power supply 22 to turn on a selected UV lamp 21 of photo-ionization source 20. The photon emissions from the selected UV lamp 21 ionize molecules in the sample gas introduced into ionization chamber 14 and thus produce ions and electrons. Repelling electrode 28 repels the ions with a selected polarity (e.g., positive ions) towards ion shutter 18, which is between ionization chamber 14 and drift tube 16. Controller 24 can operation shutter 18 for broadband detection or selective detection. Ion shutters are well known in the art and typically include two closely space electrodes. To shut ion shutter 18, a potential differences between the two electrodes creates a strong electric field that opposes a flow of electrons from the ionization chamber 14 to drift tube 16. Turning off or reversing the potential difference between the plates of shutter 18 opens shutter 18.

For broadband detection, ion shutter 18 is always open so that ions continually pass from ionization chamber 14 to drift tube 16 as the ions are created. The ions drift down drift tube 16 where collector electrode 32 collects and measures all ion species simultaneously. The ion current through collector electrode 32 indicates the total number of ions of all types created. With broadband detection, PID 10 can give a primary alarm upon detecting a threshold level of compounds from a group of target compounds. After that, PID 10 can be switched to selective detection to further identify and measure specific target compounds.

For selective detection, a pulse signal opens ion shutter 18 for a very short period (e.g., 0.2 ms) and then closes ion shutter 18. While ion shutter 18 is open, a thin layer of ions passes through ion shutter 18. The time at which ion shutter 18 closes after being open is set as time zero for an ion mobility measurement. After ion shutter closes, the thin layer of ions drifts through drift tube 16 towards collector electrode 32, and different ion species separate from each other because of the differences in mobilities for different ions. An aperture grid electrode 34 immediately before collector electrode 32 prevents the buildup of ion charge on the collector electrode 32, imparts energy to the ions to increase collection efficiency, and filters out artifact signals that arise from the opening and closing of ion shutter 18. An optional secondary ion shutter 26, which is also coupled to controller 24, can be used before aperture grid electrode 34 to selectively pass or block the ions in a predetermined drift time range. A signal processing system 52 coupled to collector electrode 32 measures the ion current versus time. The different drift times for different ions distinguish different chemicals based on ion mobility. The intensity of the detected signal can be used to quantify the concentration of the chemical species in the sample gas. Processing system 52 identifies the peaks in the measured ion current versus time response of detector 10 and compares the timing of the peaks to a data base of peak patterns for different target gases. The magnitudes of the peaks can be used both to identify the ions and to quantify the amount of the identified compound in the original sample. An exemplary embodiment of processing system 52 includes a microcontroller such as a Motorola 6811C16 that executes suitable firmware for identification and concentration measurements for target gases. To reduce system components, the function and structure of processing system 52 and controller 24 can be merged into a single processing unit that executes the appropriate firmware.

Figure 2A:
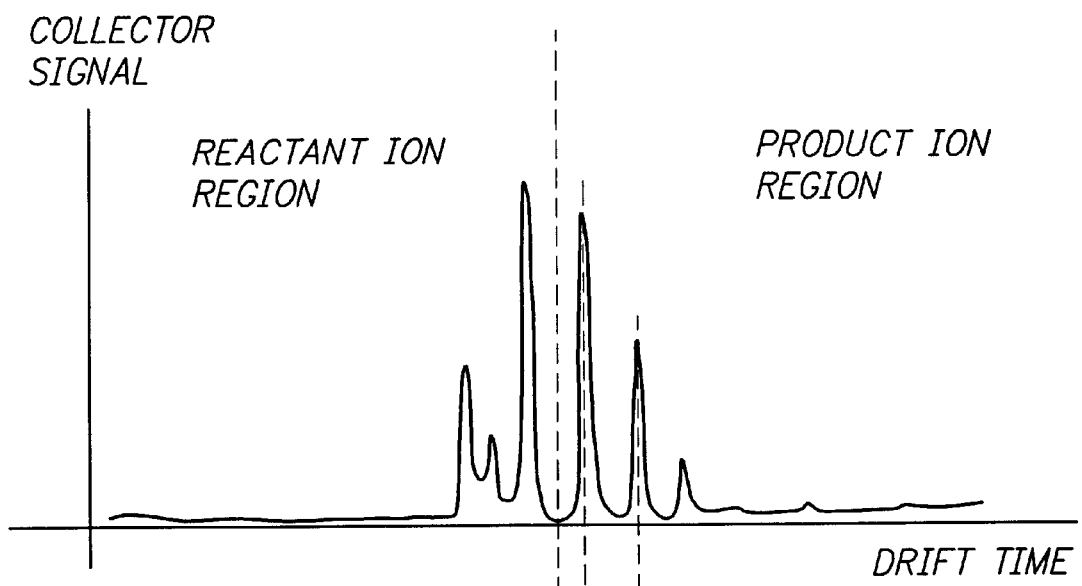
FIGS. 2A and 2B are the plots of ion mobility detector response versus drift time using a conventional radioactive ionization source and a photo-ionization source, respectively.
Figure 2B:
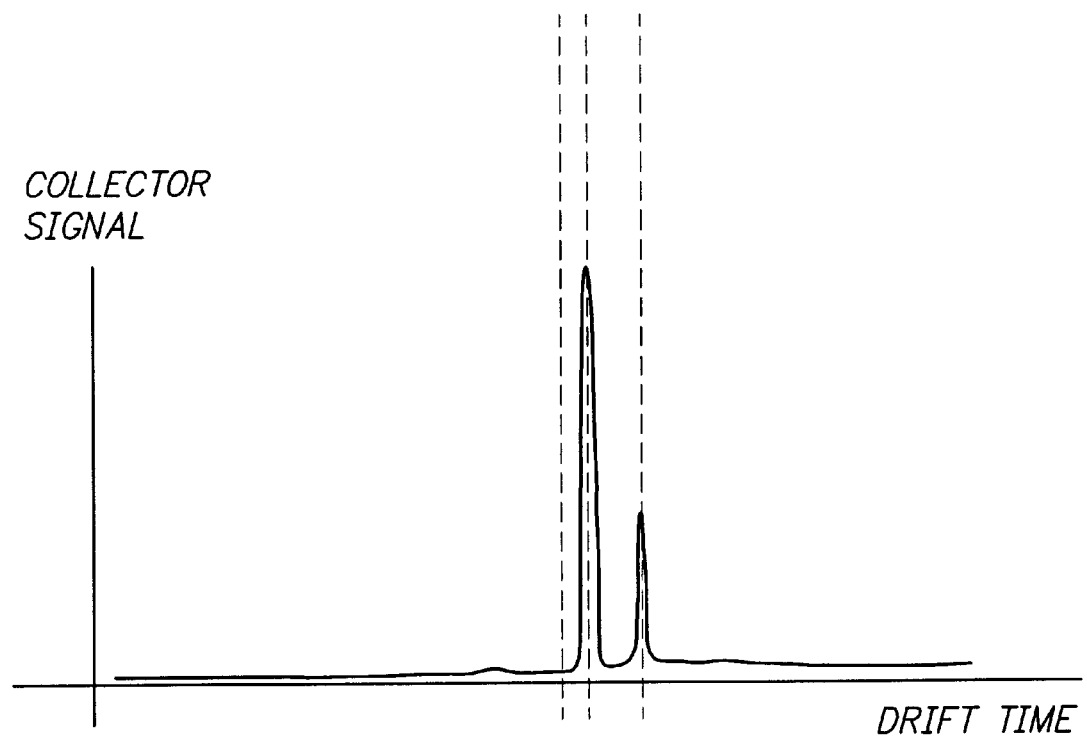

Using UV lamps 21 as the ionization source simplifies the ion mobility spectrum (i.e., the collected ion current versus drift time) when compared to a similar signal obtained with a radioactive $^{63}Ni$ chemical ionization source. FIG. 2A is a plot of the ion-mobility spectrum for benzene in air obtained with a $^{63}Ni$ foil as the ionization source, and FIG. 2B is a plot of the ion mobility spectrum for the same sample of benzene in air obtained with a UV lamp having a maximum photon energy of 10.6 eV as the ionization source. For both FIGS. 2A and 2B, all the necessary experimental conditions are the same except the ionization source, and the drift tube is in accordance with the above described embodiment of the invention. Comparison of FIGS. 2A and 2B shows that the ion mobility spectrum using a photo-ionization source is much simpler than that obtained using a $^{63}Ni$ foil as foil. The spectrum (FIG. 2A) obtained with a $^{63}Ni$ foil includes reactant ion peaks not present in the spectrum (FIG. 2B) obtained with a photo-ionization source. The reactive ion peaks result from ions of the constituents of air and ions that result from chemical reactions of these reactive ions. The simpler ion mobility spectrum of FIG. 2B results from producing fewer species of ions and the lack of reactive ions that chemically react with other constituents of the gas sample. The simpler ion mobility spectrum is less likely to produce overlapping current peaks and makes the spectrum of the target ions easier to identify.

Figure 3A:
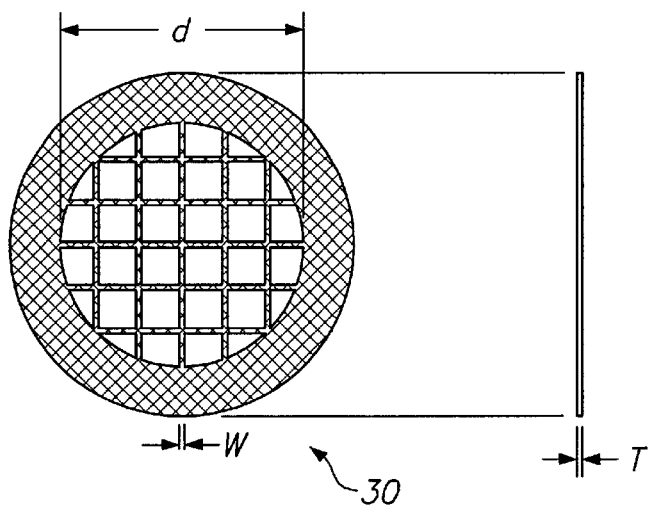
FIGS. 3A, 3B, and 3C show alternative electrodes for drift tubes in accordance with embodiments of the invention.
Figure 3B:
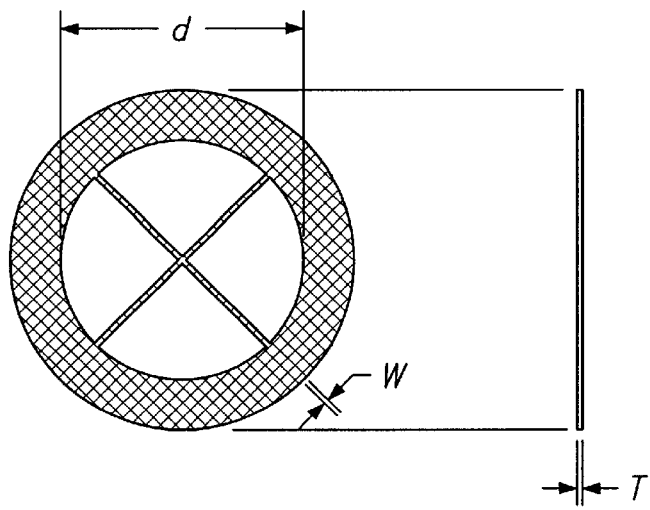
Figure 3C:
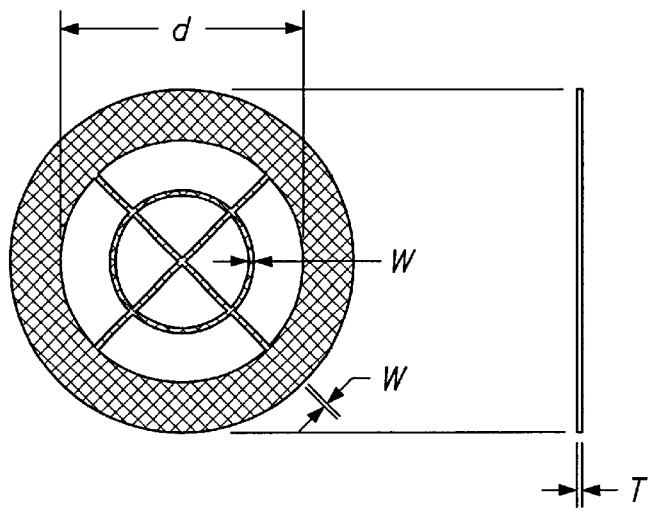

Electrodes 30 in accordance with an embodiment of the invention are thin mesh plate electrodes, in contrast to the traditional thick cylindrical hollow ring electrodes in drift tubes. FIG. 3A shows an embodiment of electrode 30 including two groups of parallel solid grid bars. Each group divides a diameter d of an inner hollow circle into sections that are preferably of equal length. These two groups of solid grid bars are preferably perpendicular to each other as shown in FIG. 3A. If each group only includes one solid grid bar as shown in FIG. 3B, the grid is actually a cross. In another exemplary embodiment, a series of concentric internal rings can also divide the diameter d of the hollow circle into sections (equal in length preferred) and a centered cross or another spoke-like pattern of metal supports the concentric rings. FIG. 3C shows such a configuration with only one internal ring. All electrodes 30 have the same configuration, and grid bars of the electrodes 30 are aligned.

In the exemplary embodiment of the invention, the diameter d of the inner hollow circle is about 18 mm, which is less than that of drift tube 16. The thickness T of electrodes is about 0.1 to 0.2 mm, and the width W of the solid grid bars or rings is also about 0.1 to 0.2 mm. The grids with suitable numbers of such solid grid bars still have nearly 95% open cross-sectional area. Thus, from a geometric point of view, such configurations do not significantly affect passing efficiency of ions in drift tube 16. However, compared with the traditional configuration, the new electrode configurations provide electric fields that are more uniform radially and axially. As a result, the peak broadening due to the variation of the electric field is less. This helps to reduce the interference between signals corresponding to different ions. In addition, electrodes 30 can provide a stronger electric drift field from the same applied voltage. Accordingly, with the same drift time and an improved peak resolution, drift tube 16 using electrodes 30 in accordance with an embodiment of the invention can use lower total voltage drop to sustain the required electric field. With the same total voltage level and the same drift time level, a drift tube in accordance with the invention can be longer to increase drift time and further improve the peak resolution.

Figure 4A:
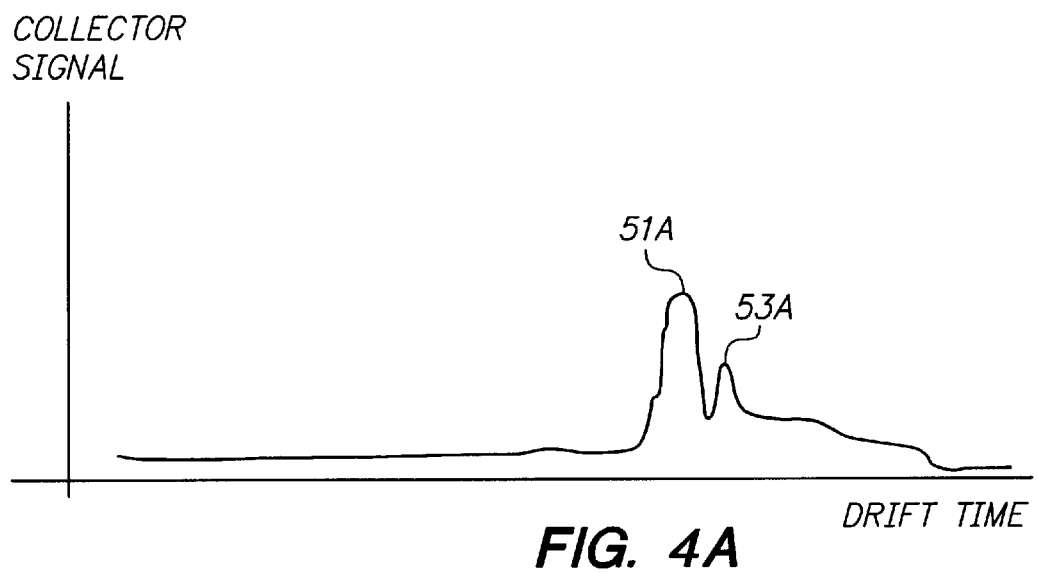
FIGS. 4A and 4B are the plots of detector response versus drift time respectively using a conventional drift tube and a drift tube in accordance with an embodiment of the present invention.
Figure 4B:
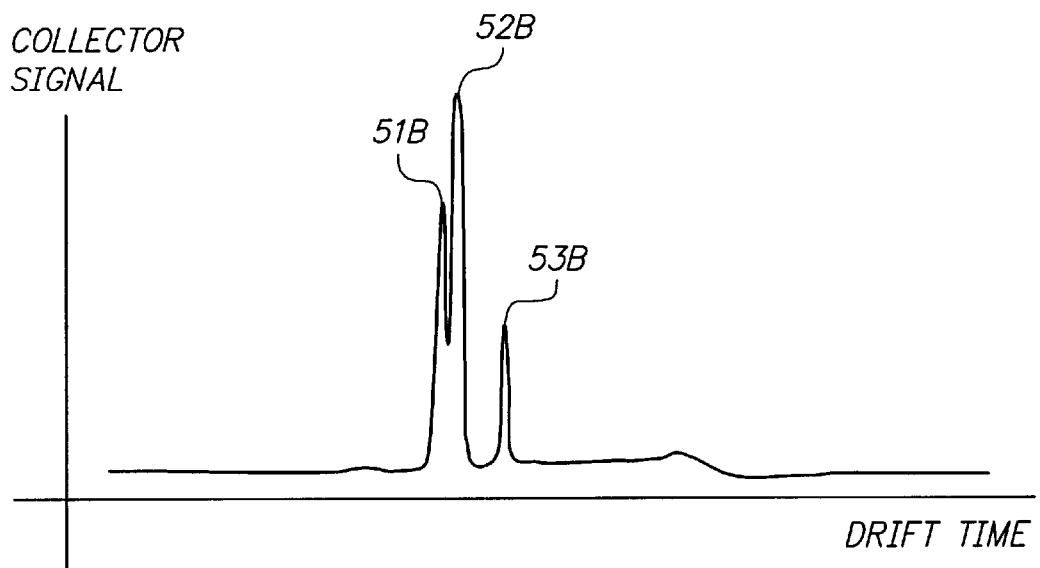

FIGS. 4A and 4B show plots of the spectra for ammonia in air obtained with a traditional drift tube and a drift tube in accordance with an embodiment of the invention, respectively. The total high voltage, the inner diameter and total length of the drift tube, the PI source, and all the other necessary conditions are the same for both FIGS. 4A and 4B. FIG. 4B shows that the drift times of peaks 51B, 52B, and 53B obtained with a new drift tube are shorter than the drift times for peaks 51A and 53A obtained with a traditional drift tube. The peak resolution in the response of FIG. 4B is also much better than that resolution in the response of FIG. 4A. In particular, FIG. 4B shows three peaks 51B, 52B, and 53B corresponding to ions generated from the sample and detected using a drift tube disclose herein, but FIG. 4A shows only two peaks 51A and 51B and is unable to distinguish the separate two peaks that merge to form peak 51A. The new drift tube 16 in accordance with the above-described embodiment of the invention provides narrow peaks that facilitate distinguishing the peaks of different gases. The new drift tube 16 also provides peaks with greater height, which facilitates identification of the peaks and quantitative measurements of the number of ions detected.

Figure 5A:
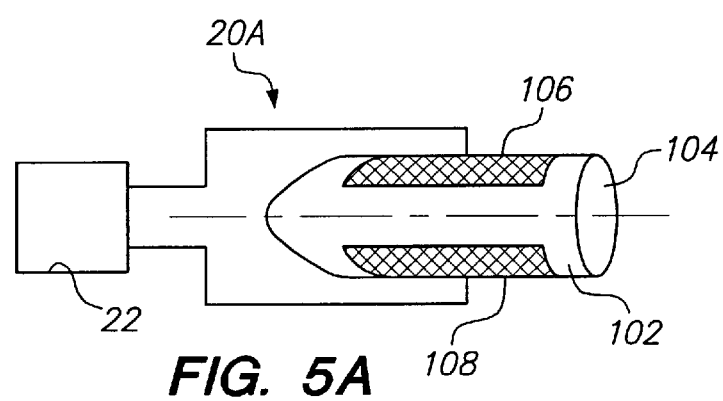
FIGS. 5A, 5B, 5C, and 5D show alternative photo-ionization sources including one or more UV lamps in accordance with embodiments of the invention.

In accordance with an aspect of the invention, an ionization source 20 can be a single UV lamp with a single UV spectrum, multiple UV lamps with different UV spectra, or a single UV lamp with multiple window zones having different UV spectra. FIG. 5A is a schematic diagram of a single energy level UV lamp 20A. UV lamp 20A comprises a glass lamp body 102, an optical window crystal 104, and two opposite plate electrodes 106, 108 surrounding lamp body 102. Lamp body 102 and window crystal 104 form a sealed envelope that encloses gases in which glow discharge can be induced. The sealed envelope may for example trap inert gases such He, Ne, Ar, and Xe alone or in combinations at a low pressure. Optical window crystal 104 is a crystal the transmits a desired frequency band of UV light. For example, optical windows made of $Al_2O_3$, $CaF_2$, $MgF_2$, and LiF are know to transmit UV light which photon energies respectively up to 8.4 eV, 9.8 eV, 10.6 eV, and 11.7 eV. The UV spectrum of a lamp can also be changed by adding a coating to window 104. Generally, the gases in lamp body 102 and the composition of window crystal 104 are selected according to a desired maximum photon energy from UV lamp 20A. AC power supply 22 drives UV lamp 20A with an AC voltage of about 300 to 500 V at a frequency of 50 to 500 kHz to induce and maintain a glow discharge process in the gases trapped in lamp body 102.

Figure 5B:
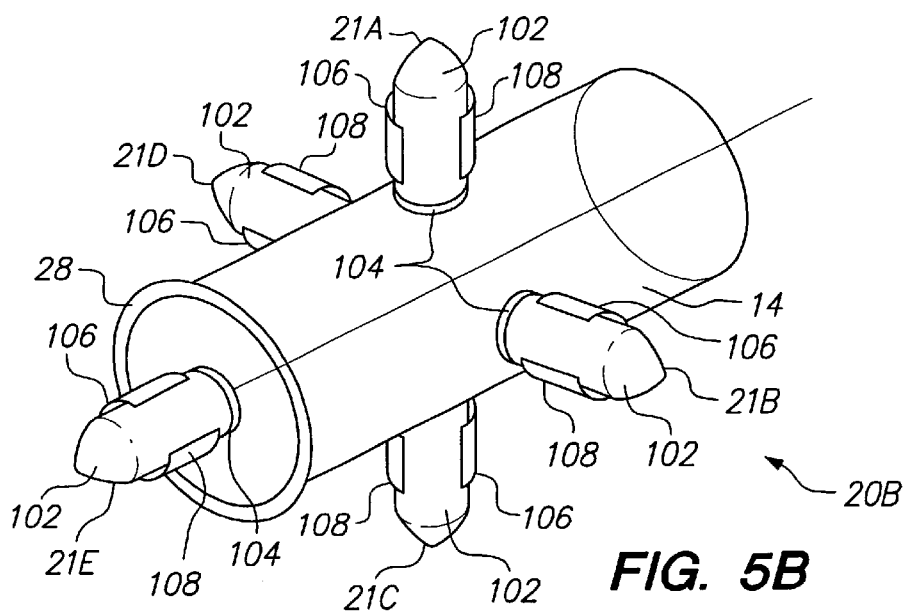

FIG. 5B shows a photo-ionization source 20B having multiple UV lamps. In FIG. 5B, five UV lamps 21A to 21E of different energy levels are mounted ionization chamber 14. Each of lamps 21A to 21E is substantially identical to lamp 20A of FIG. 5A and includes a lamp body 102, a window crystal 104, and electrodes 106 and 108 coupled to AC power supply 22. Lamps 21A to 21E differ from each other in the enclosed gas or window crystal 104 so that each of lamps 21A to 21E produces UV light having a different maximum photon energy. In operation, AC power supply 22 powers only one of UV lamps 21A to 21E at a time to select the maximum photon energy available for ionizing gas molecules. Lamps 21A to 21D produce UV light that propagates substantially perpendicular to the axis of ionization chamber 14 and drift tube 16. UV lamp 21E directs UV light along the axis of ionization chamber 14 and drift tube 16. Generally, gases in ionization chamber 104 absorb the UV light from lamp 21E within a short distance from window 104 so that none of the UV light reaches the drift tube 16. However, since the drift gas flowing through of drift tube 16 is purified air, typically the ions in drift tube 16 are the only ionizable compounds that might be affected if UV light reached drift tube 16.

Figure 5C:
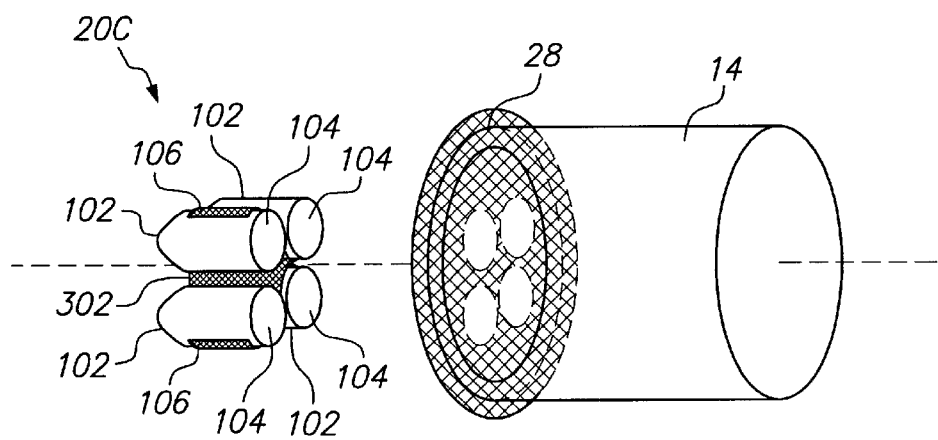

FIG. 5C shows an expanded view of a configuration for another photo-ionization source 20C using multiple UV lamps. Photo-ionization source 20C includes several UV lamps mounted together with a common electrode 302. Each of the UV lamps is otherwise the same as lamp 20A of FIG. 5A but includes a different gas or a different window crystal 104 to produce a different UV light spectrum. The UV lamps are mounted on the axis of ionization chamber 14 as an example but may be mounted to direct UV light in another direction through ionization chamber 14.

Figure 5D:
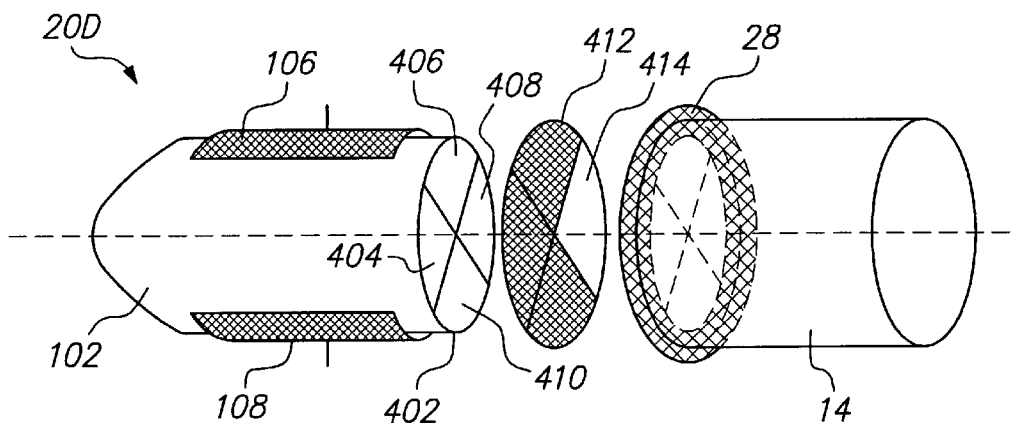

FIG. 5D shows a photo-ionization source 20D using a single UV lamp with a window crystal 402 including of multiple window zones 404, 406, 408, 410. Each zone transmits UV light having different maximum photon energy. For example, window zones 404, 406, 408, and 410 transmit photons having energies up to 8.4 eV, 9.8 eV, 10.6 eV, and 11.7 eV, respectively. The different zones can be created using different crystal materials or different coatings on optical window 402. The zones are preferably of the same size. A zone selector 412, which has an open area 414 no bigger than the area of one window zone, is between window crystal 402 and ionization chamber 14. Rotating zone selector 412 selects which one of window zones 404, 406, 408, and 410 transmits UV light into ionization chamber 14.

Figure 6A:
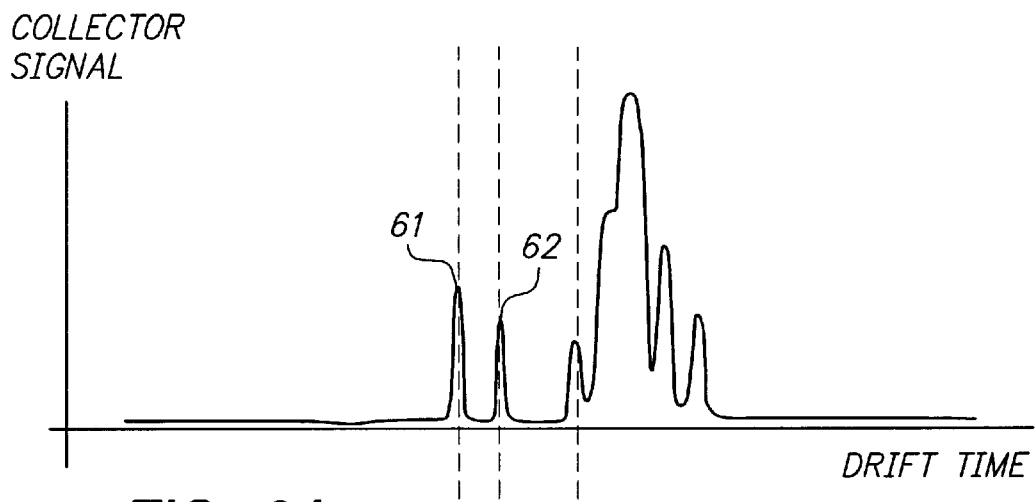
FIGS. 6A and 6B are the plots of detector responses versus drift time using UV lamps with different maximum photon energies.
Figure 6B:
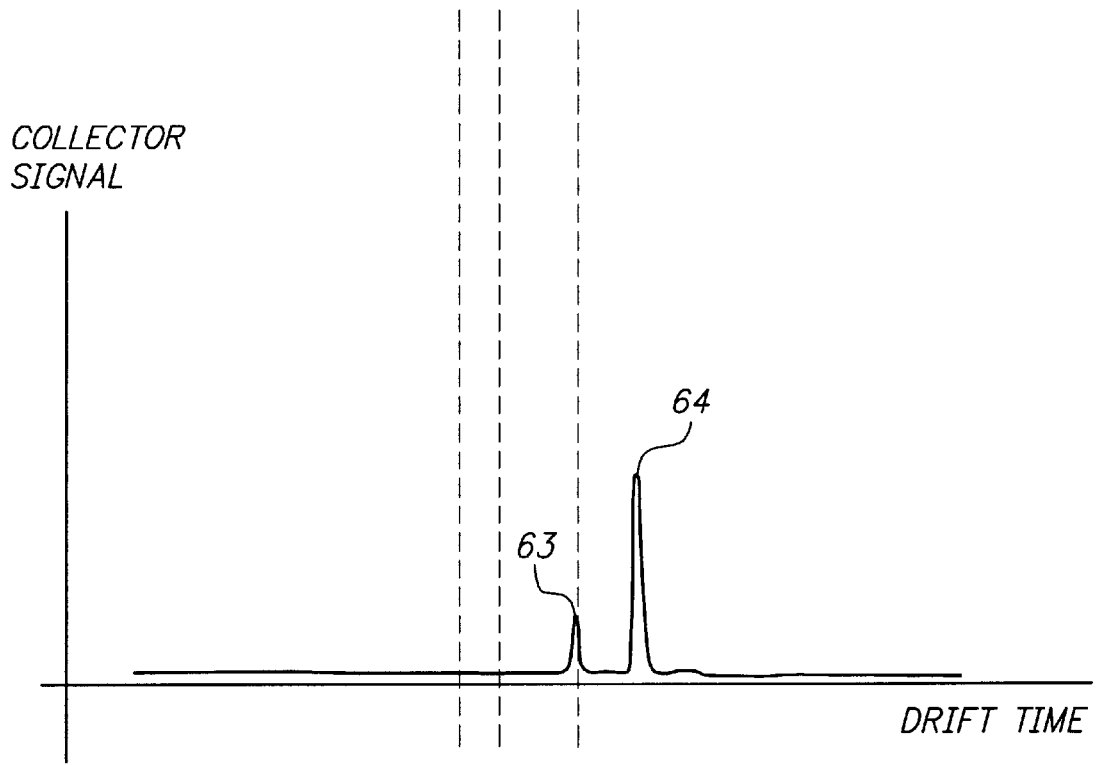

Using multiple UV spectra having different maximum photon energies increases the tunable selective capabilities of the PID. FIGS. 6A and 6B show the selective detection of phosphine ($PH_3$), which has an ionization potential of 9.87 eV, and 1-1-dimethyl hydrazine (UDMH, $C_4H_8N_2$), which has an ionization potential of 7.28 eV, from a gas mixture. FIG. 6A corresponds to a measurement where the maximum photon energy is 10.6 eV, and FIG. 6B corresponds to a measurement where the maximum photon energy is 8.2 eV. Theoretically, all of the chemicals with ionization potentials less than 10.6 eV can be ionized by turning on a 10.6 eV UV lamp as the ionization source. Peaks 61 and 62 in FIG. 6A are a signal indicating phosphine, which has a relatively short drift time. The sample, in this case, does not contain compounds having similar drift times which interfere with detection of the phosphine. However, at photon energy 10.6 eV, the signals of other ions from the sample overlap the signal of 1-1-dimethyl hydrazine. When an 8.2 eV UV lamp is the ionization source, only the components with ionization potentials less than 8.2 eV can be ionized. As a result, a significantly simplified ion-mobility spectrum shown in FIG. 6B more clearly has peaks 63 and 64 identifying 1-1-dimethyl hydrazine.

Figure 7A:
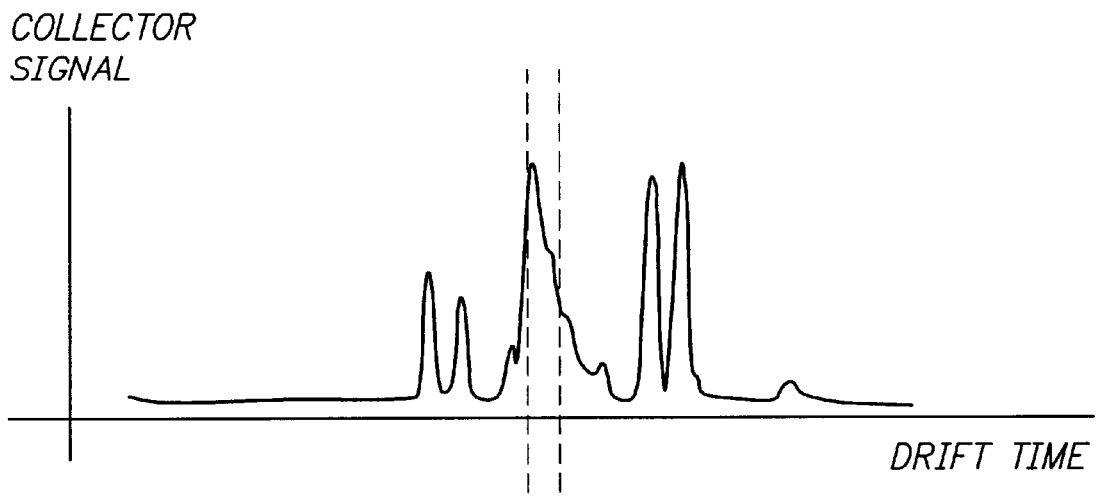
FIGS. 7A and 7B are the plots of detector responses versus drift time respectively with and without a selective chemical filter.
Figure 7B:
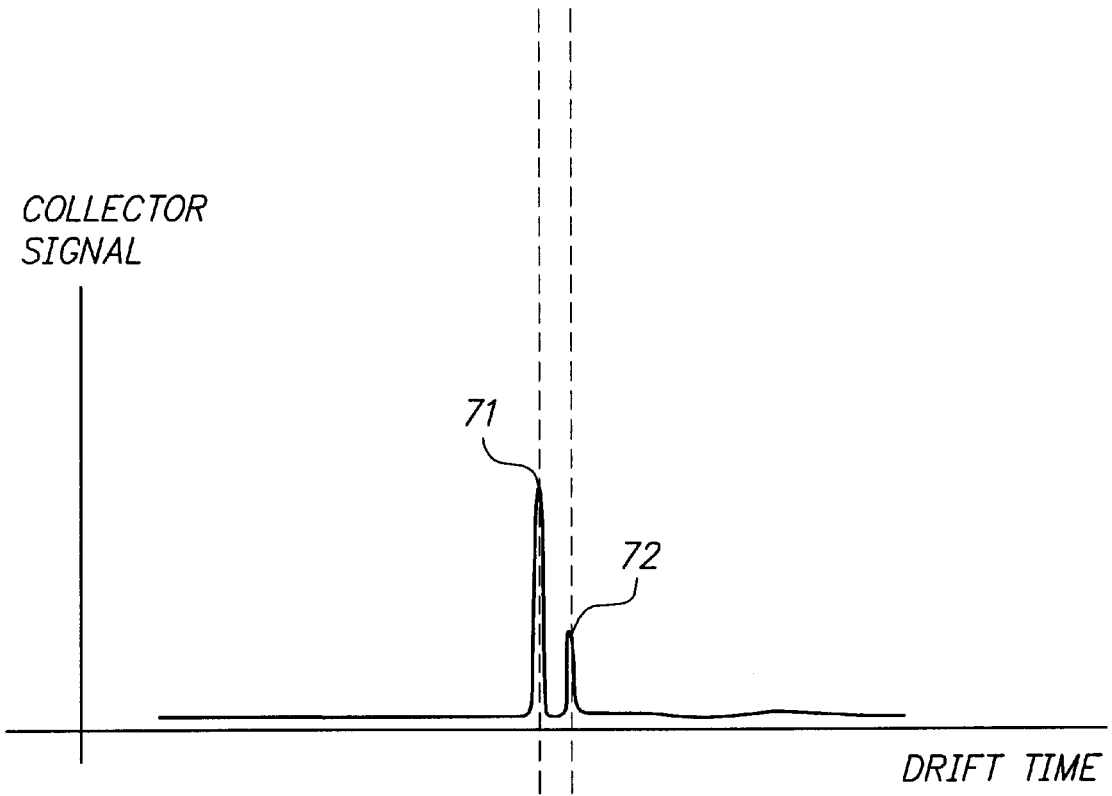

Chemical filtering device 42 (FIG. 1) can further reduce the overlap of the mobility signals of specified target components and signals of other components which are not of interest. For example, a suitable filter 42 passes the target components to ionization chamber 14 but removes expected coexisting components that might interfere with the detection of the target components. Chemical filtering device 42 can be a single filter or a series of chemical selective filters or membranes. Such chemical selective filters or membranes include all types known in the art including filters based on adsorption, absorption, size exclusion, and/or reaction. FIGS. 7A and 7B show an example of the effect of selective detection of benzene in a complicated air sample containing n-butane, iso-butane, diethyl benzene, ethyl benzene, methyl (tert.) butyl ether, momostyrene, pentane, toluene and xylene. The ionization potential of benzene is 9.25 eV, which is higher than the ionization potentials of many of the compounds indicated above. Accordingly, if the photon energy is high enough to ionize benzene, many of the interfering compounds will also be ionized. FIG. 7A shows the mobility signal for the unfiltered sample (without filter 42), and FIG. 7B shows the mobility signal using a PID with a filter 42 that selectively allows benzene to pass through while removing other interfering VOCs (Volatile Organic Compounds). Without filtering, the signal of benzene is difficult to identify, as can be seen from FIG. 7A. A chemical filter of the type described above significantly simplifies the ion mobility spectrum and allows easy detection of peaks 71 and 72 indicating the presence of benzene in the complicate sample.

Although the invention has been described with reference to particular embodiments, the description is only an example of the invention's application and should not be taken as a limitation. Various adaptations and combinations of features of the embodiments disclosed are within the scope of the invention as defined by the following claims.

We claim:

1. A photo-onization detector comprising:
   an ionization chamber;
   a drift chamber adjacent the ionization chamber;
   a photo-ionization source mounted to illuminate the ionization chamber and generate ions from a sample in the ionization chamber, wherein the photo-ionization source produces a plurality of UV spectra for illumination of the ionization chamber; and
   a control coupled to the photo-ionization source, wherein the control selects which of the plurality of UV spectra the photo-ionization source provides for illumination during a measurement using the drift chamber to determine ion mobility;
   wherein the photo-ionization source comprises a UV lamp;
   the UV lamp has a window that transmits UV light for illumination of the ionization chamber;
   the window comprises a plurality of window zones, each window zone transmitting a corresponding one of the plurality of UV spectra;
   wherein the control comprises a zone selector mounted between the window and the ionization chamber, the zone selector being movable to position an opening in the zone selector so that the zone selector blocks UV light to the ionization chamber from all window zones except one.

2. The detector of claim 1, wherein the photo-ionization source comprises a UV lamp.

3. The detector of claim 2, wherein:
   the UV lamp has a window that transmits UV light for illumination of the ionization chamber; and
   the window comprises a plurality of window zones, each window zone transmitting a corresponding one of the plurality of UV spectra.

4. The detector of claim 1, wherein the photo-ionization source comprises a plurality of UV lamps, each UV lamp generating a corresponding one of the plurality of UV spectra.

5. The detector of claim 4, wherein the control comprises a circuit that selects which one of the plurality of UV lamps is powered for the measurement.

6. The detector of claim 1, further comprising:
   a gas sample inlet in communication with the ionization chamber for introducing a sample gas into the ionization chamber;
   a drift gas inlet in communication with the drift chamber for entering a drift therethrough; and
   an exhaust passage in communication with the ionization chamber for exhausting the sample gas and the drift gas.

7. The detector of claim 6, further comprising:
   an air inlet for air from an ambient surrounding the detector; and
   a purifier between the air inlet and the drift gas inlet, wherein the drift gas comprises purified air from the air purifier.

8. The detector of claim 7, further comprising a branch including a first branch leading to the air inlet, a second branch leading to the purifier, and a third branch leading to the gas sample inlet.

9. The detector of claim 8, further comprising a chemical filter between the third branch and the gas sample inlet.

10. The detector of claim 6, further comprising:
    an inlet for an unfiltered sample gas; and
    a chemical filter between the inlet and the gas sample inlet, wherein the chemical filter filters the unfiltered sample gas to produce the sample gas introduced into the ionization chamber through the gas sample inlet.

11. The detector of claims 6, further comprising a gas chromatographic column coupled to the sample inlet, wherein the gas chromatographic column separates and input gas into components and provides the components as the gas sample at different times.

12. The detector of claim 1, wherein the drift chamber comprises a plurality of electrodes biased to produce an electric field in a direction opposite a flow of a drift gas though the drift chamber to the ionization chamber.

13. The detector of claim 12, wherein each of the electrodes comprises a projection extending into the drift chamber.

14. The detector of claim 12, wherein each of the electrodes comprises a mesh extending across the drift chamber.

15. The detector of claim 12, wherein each electrode is less than 1 mm thick.

16. The detector of claim 1, further comprising:
    an ion shutter between the ionization chamber and the drift chamber;
    a repelling electrode in the ionization chamber, the repelling electrode being biased to repel ions towards to the ion shutter;
    a collector electrode in the drift chamber, the collector electrode collecting ions that travel across the drift chamber; and a plurality of electrodes in the drift chamber, the plurality of electrodes being biased to form a uniform electric field between the ion shutter and the collector electrode.

17. The detector of claim 16, further comprising:

a circuit that electrically pulses the ion shutter to allow intermittent passage of ions therethrough; and a signal processing system coupled to the collector electrode, wherein the signal processing system detects ion current in the collector electrode and identifies compounds from times between pulsing of the ion shutter and arrival of ions at the collector electrode.

* * * * *